(12) United States Patent
Witt et al.

(10) Patent No.: US 8,515,587 B2
(45) Date of Patent: Aug. 20, 2013

(54) CONFIGURING A PHYSICAL CONDITION AT A SOURCE TO OBTAIN A DESIRED PHYSICAL CONDITION AT DESTINATION

(75) Inventors: Klaus Witt, Keltern (DE); Herbert Anderer, Waldbronn (DE); Alwin Ritzmann, Waldbronn (DE); Dominik Ruf, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 511 days.

(21) Appl. No.: 12/234,621

(22) Filed: Sep. 20, 2008

(65) Prior Publication Data

US 2009/0076631 A1   Mar. 19, 2009

(51) Int. Cl.
*G05D 11/02* (2006.01)

(52) U.S. Cl.
USPC ............................. 700/285; 700/266

(58) Field of Classification Search
USPC ............... 700/17, 282, 285; 73/19.02, 23.35, 73/53.01; 210/198.2, 635, 656; 715/772; 137/2; 702/45–49
See application file for complete search history.

(56) References Cited

U.S. PATENT DOCUMENTS

| | | | |
|---|---|---|---|
| 4,607,342 A * | 8/1986 | Seiden et al. ................. | 700/285 |
| 4,618,935 A * | 10/1986 | Schwartz ..................... | 700/285 |
| 4,918,935 A | 4/1990 | Trent | |
| 5,072,404 A * | 12/1991 | Schmitzer et al. ............ | 700/285 |
| 7,167,776 B2 * | 1/2007 | Maharajh et al. ............. | 700/266 |
| 7,400,940 B2 * | 7/2008 | McRae et al. ................. | 700/266 |
| 2002/0035412 A1 | 3/2002 | Kircher et al. | |
| 2005/0143866 A1 | 6/2005 | McRae et al. | |
| 2006/0047368 A1 * | 3/2006 | Maharajh et al. ............. | 700/283 |
| 2010/0057264 A1 * | 3/2010 | Kircher et al. ................ | 700/285 |

OTHER PUBLICATIONS

John W. Dolan, "Dwell Volume Revisited", LCGC North America. vol. 24, No. 5, May 2006, pp. 458 to 466.
German Office Action for Application No. 10 2009 029 028.1 dated Oct. 26, 2011, with English Translation (9 pages).
G. Hendriks, et al. "New practical algorithm for modeling retention times in gradient reversed phase high performance liquid chromatography" Journal of Chromatography A, 1089 (2005), p. 193-202.

* cited by examiner

*Primary Examiner* — Dave Robertson

(57) ABSTRACT

An apparatus for determining an operation mode of a device, wherein the device is capable of adjusting a physical condition at a source position to correspondingly influence a physical condition at a destination position, the apparatus comprising a determining unit adapted for determining the operation mode by defining a time dependency of the physical condition at the source position so that a target time-dependency of the physical condition is obtained for the destination position, the target time-dependency representing a resultant variation of the physical condition over time.

18 Claims, 7 Drawing Sheets

US 8,515,587 B2

CONFIGURING A PHYSICAL CONDITION AT A SOURCE TO OBTAIN A DESIRED PHYSICAL CONDITION AT DESTINATION

BACKGROUND ART

The present invention relates to the operation of fluidic devices.

Fluidic devices are applied to execute various measurement tasks in order to measure any kind of physical parameter. Each fluidic device may have a specific driver with device specific commands. A programming software allows a user to design an operation mode of the fluidic device. As a result of such a design, the fluidic device may be operated in accordance with the designed operation mode.

More particularly, in liquid chromatography, a fluidic analyte may be pumped through a column comprising a material which is capable of separating different components of the fluidic analyte. Such a material, so-called beads, may be filled into a column tube which may be connected to other elements (like a control unit, containers including sample and/or buffers). Upstream of a column, the fluidic analyte is loaded into the liquid chromatography apparatus. A controller controls an amount of fluid to be pumped through the liquid chromatography apparatus, including controlling a composition and time-dependency of a solvent interacting with the fluidic analyte. Such a solvent may be a mixture of different constituents. The supply of these constituents for subsequent mixing is an example of an operation to be designed by an operator of a liquid chromatography device.

John W. Dolan, "Dwell Volume Revisited", LCGC North America. Volume 24, No. 5, May 2006, pages 458 to 466 discloses that the practical impact of a system dwell volume on retention and resolution in liquid chromatography is not something to take lightly. It is unfortunate that many chromatographers ignore dwell volume considerations when developing and transferring gradient LC methods.

Hence, a conventional operation mode adjustment system for a device may lack accuracy.

DISCLOSURE

It is an object of the invention to provide an accurate operation mode adjustment system. The object is solved by the independent claims. Further embodiments are shown by the dependent claims.

According to an exemplary embodiment, an apparatus (such as a computer or a workstation) for determining an operation mode of a device is provided, wherein the device is capable of adjusting a physical condition at a source position (such as a position at which several components of a solvent are supplied to a pump and mixing system) to correspondingly influence a physical condition at a destination position (such as an outlet of a mixing system in fluid communication with or upstream of a separation column), the apparatus comprising a determining unit (such as a processor) adapted for determining the operation mode by defining a time dependency of the physical condition at the source position so that a target time-dependency of the physical condition (such as a desired time-dependent concentration function) is obtained for the destination position, the target time-dependency representing a resultant variation of the physical condition over time.

According to another exemplary embodiment, a method of determining an operation mode of a device is provided, wherein the device is capable of adjusting a physical condition at a source position to correspondingly influence a physical condition at a destination position, the method comprising determining the operation mode by defining a time dependency of the physical condition at the source position so that a target time-dependency of the physical condition is obtained for the destination position, the target time-dependency representing a resultant variation of the physical condition over time.

According to still another exemplary embodiment of the present invention, a software program or product is provided, preferably stored on a data carrier, for controlling or executing the method having the above mentioned features, when run on a data processing system such as a computer.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of device operation management. The device operation management scheme according to an embodiment of the invention can be performed or assisted by a computer program, i.e. by software, or by using one or more special electronic optimization circuits, i.e. in hardware, or in hybrid form, i.e. by means of software components and hardware components.

The term "operation mode" may particularly denote a workflow, an algorithm or a set of operation parameters defining as to how a device or particularly a fluidic device is to be operated or run. Thus, the operation mode may include a complete set of data which, when provided to the fluidic device, defines a dedicated operation of this fluidic device.

The term "device" may particularly denote any technical apparatus. The term "fluidic device" may particularly denote any apparatus which involves the transport, analysis or processing of a fluid. A fluid may denote a liquid, a gas or a combination of a liquid and a gas, and may optionally also include solid particles. Such a fluid may comprise a fluidic solvent and/or a fluidic sample under analysis. Examples for fluidic devices are life science apparatuses or any other biochemical analysis system such as a separation device for separating different components of a sample, particularly a liquid chromatography device.

The term "source position" may particularly denote an initial position along a working path of a device, particularly a position within a fluidic path of a fluidic device at which one or more fluidic components such as solvent components or constituents are supplied for subsequent mixing. It is in many cases easy for a user to properly define concentration of such constituents or components at a source or delivery position since this is the position where the components are actually delivered under precise control of a user.

The term "destination position" may particularly denote a final position along a working path of a device, particularly a position within a fluidic device which is spatially separated from the source position and which can be a position in a flow path downstream of the source position, i.e. after a well-defined processing of the fluidic components supplied at the source position. Between the source position and the destination position, the fluidic components may be subject to various (for instance controllable and non-controllable, desired and non-desired, analytically modellable and non-modellable) manipulation effects such as delay effects and broadening and mixing effects acting on the fluidic stream which may originate from one or more dead volumes such as conduit volumes of a liquid chromatography device, friction, formation of temperature or velocity profiles, or the like.

The term "time sequence" may particularly denote a time scheme defining at which points of time which physical conditions are set, particularly a time scheme defining at which points of time which relative concentrations of multiple fluidic components are to be supplied at a source position.

The term "target time dependency" may particularly denote a desired time dependency of a physical condition, particularly of a concentration of individual components of the fluidic sample or solvent at the destination position which a user wishes to adjust. Such a target time dependency at a destination position may significantly differ regarding one or more parameters from a corresponding characteristic at the source position because of several effects acting on a fluidic sample solvent moving along a processing volume from the source position to the destination position.

According to an exemplary embodiment, an operation mode or control sequence may be negotiated or agreed upon between a processor entity and a user in a man-machine dialogue. The resulting operation mode may be adjusted so that a defined target behaviour is obtained at a destination position of a working path of a device which position cannot or cannot easily be controlled directly. By taking such a measure, a flow ramp, a temperature profile, a mixture composition, etc. may be adjusted at the destination by evaluating as to how a corresponding physical condition has to be set at the source position to achieve the desired result at the destination.

More specifically, according to an exemplary embodiment, a user convenient system for assisting a user in setting an operation mode for a fluidic device is provided. Such a system allows the user to accurately design a desired time dependency of partial concentrations of a mixture of different fluids at a destination position such as a head or inlet of a chromatographic column. When such a desired profile is defined by a user, the system may automatically calculate, for instance by modeling the real physical conditions (such as dead volume, etc.) in the fluidic device, an easily executable recipe according to which the different constituents are to be supplied at the source position (particularly at which partial concentrations and with which time dependency) so that the input target time dependency of the concentration profile of the mixture will be obtained at the destination position. Thus, the in many cases complex physical processes between source position and destination position of a fluidic device need not be known to or considered by the user for designing an analysis or experiment, thereby allowing even an unskilled user to simply define what a user wants and outputting a corresponding recipe to be followed (by for instance controlling the device) so that the user will actually obtain the desired result.

In the following, further exemplary embodiments of the apparatus will be described. However, these embodiments also apply to the method, to the software program and to the software product.

The fluidic device may be capable of mixing at least two fluidic components at the source position and may be capable of transporting the mixture to the destination position, wherein the determining unit may be adapted for determining the operation mode by defining a time sequence of supplying the at least two fluidic components at the source position so that a target time-dependency of a concentration profile of the mixture is obtained for the destination position, the target time-dependency representing a concentration variation of the mixture over time. In such a context, any undesired manipulation of a mixture composition may be at least partially compensated.

Additionally or alternatively, the fluidic device may be capable of supplying a fluid with a definable temperature at the source position and may be capable of transporting the fluid to the destination position, wherein the determining unit may be adapted for determining the operation mode by defining a temperature profile of supplying the fluid at the source position, or by supplying a certain power to the fluidic device at a source position, so that a target time-dependency of a temperature profile of the fluid is obtained for the destination position, the target time-dependency representing a temperature variation of the fluid over time. In such a context, any undesired manipulation of the temperature of the fluid along a flow path may be at least partially compensated. In a scenario in which for instance the temperature is programmed as a fast ramp, this may have the effect, particularly in case of a large flow, that the actual temperature is delayed. Also in such a scenario, it may be possible to predict the true temperature profile to compensate for such delay effects.

Additionally or alternatively, the fluidic device may be capable of supplying a fluid with a definable flow profile at the source position and may be capable of transporting the fluid to the destination position, wherein the determining unit may be adapted for determining the operation mode by defining a flow profile of supplying the fluid at the source position so that a target time-dependency of a flow profile of the fluid is obtained for the destination position, the target time-dependency representing a flow variation of the fluid over time. In such a context, any undesired manipulation of a flow ramp or a flow rate along a flow path introduced by for instance a hydraulic capacitance may be at least partially compensated.

The determining unit may be adapted for determining the operation mode under consideration of a preknown parameterization of the fluidic device. Such a parameterization may be formed by a set of parameters indicating physical properties of the fluidic device which may have an impact on a concentration profile of multiple fluidic constituents moved from one or more source positions to one or more destination positions. Such parameters may include volumes of different fluidic paths, a pumping power of one or more pumps transporting the fluidic components through the fluidic device, dimensions (such as a diameter and/or length) of fluidic conduits which may have an impact on the broadening of the fractions of the fluidic sample, etc. Thus, a parameterization of the fluidic device may be denoted as a set of parameter values representing or defining physical effects by a number of parameters as a basis for a computer model. Parameterization of a fluidic device may allow to calculate a model of the fluidic device so as to computationally arrive at the desired time dependency of the individual concentrations at the source position which have to be adjusted to obtain the target time dependency.

The parameterization may define one or more physical properties of the fluidic device. Such physical properties may involve a transport characteristic which may include parameters such as volumes, dimensions, values of physical parameters such as mixing behaviour, pressure drop or temperature, and/or physical effects such as a model of friction occurring in a fluidic conduit which friction effects may be modeled, for example, according to the Hagen Poiseuille law. Such a physical modeling of the procedures within the fluidic device allow to derive a difference between conditions at the input position and at the output position, which may be defined by a transfer function $Hb=output/input$.

More particularly, the parameterization may consider a size of a fluidic device (for instance a dimension of a fluidic channel), a volume of a fluid conduit (such as a dead volume) of the fluidic device, a pump performance (such as the pump power and/or pump capacity) of the fluidic device, a delay parameter (such as a delay time after switching on a fluidic device) of operating the fluidic device, a friction parameter (for instance characterizing friction between a wall of a fluidic conduit and a fluid flowing through the conduit) of operating the fluidic device, a flush performance (particularly properties related to rinsing or flushing the fluidic device before operating it or between two subsequent operations) of the fluidic device, and/or a cooperation of different components of the fluidic sample (for instance the properties of a gradient applied to a chromatographic column which, for example, may be connected to the destination.

Alternatively the transfer function can be exploited empirically by measuring the output of a certain fluidic device or complex structure, while introducing a known or likewise measured input stimulus. The transfer function then is a complex quotient of complex output function divided by the complex input function.

The operation mode may define a procedure of separating different components of fluids by the fluidic device (for example a recipe as to how to run a liquid chromatography, gas chromatography or electrophoresis experiment), a procedure of analyzing a medication (for example in a coupled liquid chromatography and mass spectroscopy device in which a metabolism of a drug in a human body may be investigated), a diagnostic procedure (for example for diagnosing a specific physiological condition based on an analysis of a sample), a procedure requiring official approval (for instance an approval procedure before the FDA, Food and Drug Administration, in the United States), a procedure of flushing the device (for example an algorithm according to which a rinse solution is supplied for conditioning or removing traces of fluids from a previous investigation, thereby suppressing undesired crosstalk or contamination), a selection of a solvent for the fluidic device (for instance selecting multiple constituents of such a solvent, their relative concentrations, etc.), a procedure of applying a concentration gradient to the fluidic device (for example to perform a liquid chromatography analysis using a chromatographic column) and/or a selection of an operation temperature (and/or other physical parameters such as pressure) for the fluidic device.

The operation mode may define a sequence of instructions providable to the fluidic device for operating the fluidic device. Such a set of instructions may be sufficient for running the fluidic device in accordance with a desired scheme.

The apparatus may comprise a user interface adapted for displaying the operation mode visually on a display (such as a liquid crystal display, a cathode ray tube, a plasma display or the like). Such a user interface may include an input unit such as a pointing device, a joystick, a keypad, a button, a touch-screen etc. allowing a user to input commands, data and instruction to the apparatus. Such a user interface may also comprise an output unit such as a display for visually displaying information to a user of the apparatus. Such an output unit may also comprise a data interface allowing a user to connect a peripheral device such as the fluidic device or a memory stick to copy a set of calculated parameters to such an apparatus. With using such a user interface, a user may design a way of operating a fluidic device in a convenient manner.

The user interface may be adapted for displaying the operation mode as graphs. Thus, with a two or three or more dimensional representation, the dependency between different parameters may be plotted in an intuitive manner in a way that the user can get a clear impression of the time dependency of an operation based on such a graph. For instance, such a graph may be a two-dimensional coordinate system having an abscissa along which the time is plotted, and may have an ordinate along which a concentration of an individual component of a multicomponent mixture may be plotted.

The user interface may be adapted for enabling a user to manipulate the operation mode. Thus, via the user interface, particularly via input elements thereof, a user may adjust the operation mode in an intuitive manner to specifically meet the user's requirements. This may allow to obtain a user-convenient user interface via which a user may precisely define which kind of experiment shall be carried out. Manipulation may be performed via a control device such as a computer mouse, a trackball, a joystick, a touch-screen or a keypad, for example controlling a pointer (such as a mouse pointer or a cursor) on a screen.

The user interface may be adapted for enabling a user to manipulate the operation mode, wherein the user interface and the determining unit may be adapted for updating or tracking a part of the operation mode upon manipulation of another part of the operation mode by the user. For instance, a user may simply vary one parameter of an operation mode and can get, in real-time, a feedback via the user interface as to how a manipulation of this parameter will affect one or more other parameters or the entire analysis. Thus, a user will get a proper impression about more critical and less critical parameters which, when being changed, have a larger or smaller impact on the corresponding experiment.

The user interface may be adapted to enable the user to define the target time-dependency of the concentration profile of the mixture at the destination position. Thus, a user does not have to design an experiment considering complex procedures within the fluidic device, but in contrast to this a user may consider the fluidic device as a "black box" which the user simply has to instruct with the user's wishes, and the system will calculate a scheme as to how a user has to operate the device in order to achieve this result. Thus, all the considerations regarding physical effects or disturbing effects between the source and the destination will be taken into account by the system so that a user does not have to care about dwell volume or similar effects.

The user interface may be adapted for enabling the user to manipulate the operation mode, wherein the user interface may be adapted to provide a visual feedback to the user in response to a modification of the operation mode. Thus, with a visual feedback system, it is possible to provide the user in an intuitive manner with the required information needed to design an experiment.

The system may be adapted as a graphical user interface (GUI) which may be denoted as a user interface which allows people to interact with electronic devices such as computers or handheld devices. Such a GUI may offer graphical icons and visual indicators as opposed to purely text-based interfaces, typed command labels or text navigation to fully represent the information and actions available to a user.

The user interface may be adapted for displaying simultaneously, i.e. on a common screen, both the time sequence of supplying the at least two fluidic components at the source position and the target time-dependency of the concentration profile of the mixture at the destination position. Therefore, in an intuitive manner, a user may get an impression of the differences between a "theoretical" or ideal way of mixing the fluids at a source location, and a "realistic" or actual way how the designed mixture of the fluid components can be obtained in the physical system at the target destination location of the fluidic device.

The determining unit may be adapted for determining the operation mode as a real operation mode or actual operation mode by substituting one of a straight curve section (that is a straight line) and an angled curve section (that is two straight lines aligned along different directions and having one point in common, therefore enclosing an angle) by a rounded curve section. Broadening effects or a velocity profile of molecules of a fluidic sample may occur which, for instance, may result from friction between individual components of the fluidic sample and walls of a fluidic conduit. Such effects may, in an actual physical experiment, result in a rounding of curve sections which, in theory or when designing an experiment, are displayed by a number of connected straight curve sections. Thus, rounding a curve in accordance with a physical model of the procedures or effects resulting from one or more laws of nature may be performed when the apparatus displays an actual time dependence of a mixture. This will give a user a more realistic impression of the actual conditions within such an apparatus.

The determining unit may be adapted for performing the substitution in accordance with a physical model of a process relating to the straight curve section or the angled curve section. Therefore, the physical procedures within the modeled fluidic device may be taken into account when calculating curves to be visually displayed to a user.

For example, the determining unit may be adapted for performing such a substitution by calculating a Bezier curve. A Bezier curve may be denoted as a parametric curve (which, generalized to higher dimensions may also be denoted as Bezier surfaces) serving as a tool to model smooth curves that can be scaled indefinitely. Such a curve may properly reflect the physical properties within a fluidic device and may allow for performing affine transformations such as translation, scaling and rotation on the Bezier curve.

The determining unit may be adapted for performing the determination by physically modeling procedures taking place in the fluidic device. Such physical models may be modeled mathematically, in an analytical, numerical, and/or phenomenological way. Considering such physical procedures may improve the accuracy of the prediction made by the apparatus. The determining unit may be adapted for performing the determination by simulating processes taking place in the fluidic device. Carrying out simulations on the basis of input data parameters may allow to properly consider the parameters indicating the apparatus, thereby allowing to obtain more predictable results. The determining unit may be adapted for performing the determination under consideration of laws of nature. For instance, accepted laws of fluid dynamics may be considered by the apparatus. Additionally or alternatively, empirically extracted transfer functions may be used to performing the determination under consideration of actual system behavior.

The apparatus may comprise an admissibility verification unit adapted for verifying whether a manipulation by a user is admissible in view of physical frame conditions and/or empirically extracted transfer functions. When a user manipulates specific parameters, the admissibility verification unit may perform a verification whether the parameter adjusted by a user is in accordance with laws of nature or is a reasonable choice in view of one or more other criteria (such as a criteria of logic). For instance, negative fluid volumes will not be accepted by the system. Furthermore, parameters (such as a too high pumping power) which are not supported by an actual fluidic device may be identified by the admissibility verification unit as well. The admissibility verification unit may distinguish between allowed parameters, non-allowed parameters and parameters which can be indicated as suspicious or questionable. Allowed parameters may be accepted without restrictions. Non-allowed parameters will be rejected. Suspicious or questionable parameters will be indicated as suspicious or questionable to a user so that a user can verify such parameters before performing the analysis with a suspicious or questionable parameter or set of parameters. Thus, the decision whether a parameter will be accepted or not by the admissibility verification unit may include physical considerations taken in accordance with physical models used by the admissibility verification unit for determining whether an adjusted parameter is acceptable from a physical or technological point of view or not.

More particularly, the admissibility verification unit may be adapted for rejecting the manipulation by the user upon detecting that the manipulation is not in accordance with physical frame conditions. This rejection may be accompanied by a feedback to the user, for instance in a visual way (such as an indicia displayed on a screen indicating that a specific operation is "not allowed") and/or in an acoustical way (for instance an acoustic tone indicating that the operation is "not allowed"). Such a visual way may be when for instance a point is easily moved by a pointing device, but stalls when a "not allowed" boundary is reached (for instance when moving a trace in negative time).

The admissibility verification unit may thus be adapted for providing feedback to the user when rejecting the manipulation by the user, the feedback including a notice that—and optionally why—the manipulation is not in accordance with physical frame conditions. Thus, the user will not only be informed that a specific operation is not allowed, but may also be informed about the physical reason why this is not allowed. Such an indication may include the notice that "the fluidic device does not support this parameter", "this parameter is not in accordance with laws of nature", "total composition can not exceed 100%", "time is not running backwards", etc.

The operation mode or "method" to be proposed by the apparatus may be indicative of a process flow of a separation method such as a chromatographic operation method. Such an operation mode may include a flush procedure, a selection solvent feature, a drive gradient feature (for driving a gradient using a chromatographic column), a further rinse feature, a selected temperature and pressure feature, etc.

According to an exemplary embodiment, real gradient programming may be made possible, by providing a user interface which may graphically display a constitution of a solvent which can be modified by a user over time to adjust the desired gradient of a concentration profile at for instance the inlet of a chromatographic column to be connected at the destination position. Thus, the time dependency of the gradient may be monitored graphically as being present at the target destination location. This may allow to provide a timetable editor allowing a user to define a procedure of supplying different components to the system. A corresponding content of data may be displayed graphically as a timetable indicative of the separation procedure. Exemplary embodiments may thus provide for a feedback system visually giving a feedback to a user what actually happens when a specific experiment is carried out. Thus, a bidirectional data communication system may be provided allowing to indicate/display also physical limits of the system (for example preventing a user to define values on a negative time axis). The system gives a user the freedom to visually parameterize a method but safely prevents the user from adjusting setpoint parameters to values, which a machine is not capable of supporting or which is not in accordance with laws of nature. For example, the graphical display of such a data space may also include further user aid such as an indication that a table value of "less than 400" is not allowed by a red line indicating that this limit may not be fallen below or undercut. According to an exemplary embodiment, real gradient programming may be made possible with a supporting user interface implementation (for instance being command line oriented, tabulated or graphical).

A corresponding timetable may be defined for a pump, a valve, a thermostat, a diode array detector, or any other component of the fluidic device as well. A temperature in a fluidic conduit, a pressure in a fluidic conduit, or the like may be considered for calculating a temperature dependency, a pressure dependency, etc. for a chromatographic column or further components arranged downstream of the mixture system. One or more wavelengths of a detector may be considered as well.

According to an exemplary embodiment, a user may be enabled to get an impression of all data required for defining an experiment and for selectively modifying individual parameters or navigating through parameters. This may include the addition or removal of a sampling point in a graph, or the like. For instance, a Bezier curve may be defined in a specific portion of a graph allowing to obtain a realistic time-dependency of a parameter with reasonable computational burden and low memory or storage requirements. Furthermore, such a Bezier curve may also allow manipulation such as stretching a curve in one dimension, compressing a curve in one dimension, zooming, unzooming or the like.

The visual feedback system according to an exemplary embodiment may provide the user with comfort and flexibility when designing an experiment in a more intuitive manner as compared to pure tables of parameter values. Such a system may be fed with data regarding the physical system to be modeled, for instance may be fed with HPLC information.

Exemplary embodiments allow to display a complex measurement system in a multidimensional manner in a way that it becomes easy for a user to navigate through such a system. A user may be aided to concentrate on what the user wishes to modify. For instance, a parameter setting or command may be allowed or a check field may be provided which can be selected or not selected by a user by activating or deactivating a corresponding flag. For example, without selecting such a flag, a change of a flow would require a manual manipulation of a gradient in order to keep the gradient volume-constant. When a corresponding flag is activated ("keep gradient volume"), this may allow to enter an interaction mode in which, when a user changes a flow, the system adjusts a gradient along time in such a manner that the gradient is kept in constant volume.

The parameterization or configuration of the fluidic device may include a flow velocity (volume per time), condition of a pump, an inner volume of a pump, a parasitic volume of fluidic conduits, thermal capacity, thermal resistance, temperature pressure correlations, delay time, and rise time of a pump, etc.

The device may be adapted for displaying a two-dimensional set of data, particularly may be adapted for displaying a measurement control curve. Such a measurement control curve (for instance a sequence of instructions defining a method such as a chromatographic method) may be provided to a measurement apparatus, for instance a life science apparatus or any other technical apparatus. Adjusting such measurement control data may be conventionally a challenge and may be significantly simplified by the intuitive user interface according to an exemplary embodiment.

The multidimensional set of data to be defined may be displayed as a graph. A graph may be denoted as a two- or three-dimensional space which correlates different parameters corresponding to different axes of a coordinate system, for instance two parameters plotted along an abscissa and an ordinate of a two-dimensional Cartesian coordinate system. Such a graph may be continuous, discontinuous, or a set of spaced points. Thus, the graph may be a continuous measurement control curve which can be differentiated at each position. However, also discontinuous graphs which cannot be differentiated at least one position can be designed according to exemplary embodiments. It is also possible that the graph is simply formed by a number of isolated and spaced points.

The fluidic device may comprise at least one of a sensor device, a test device for testing a device under test or a substance, a device for chemical, biological and/or pharmaceutical analysis, a fluid separation system adapted for separating components of a fluid, an electrophoresis device, a capillary electrophoresis device, a gel electrophoresis device, a liquid chromatography device, a capillary electrochromatography device, a gas chromatography device, an electric measurement device, and a mass spectroscopy device. Thus, exemplary application fields of a fluidic device according to embodiments are gas chromatography, mass spectroscopy, UV spectroscopy, optical spectroscopy, IR spectroscopy, liquid chromatography, capillary electrochromatography, and capillary electrophoresis bioanalysis. More generally, the device according to embodiments may be integrated in an analysis device for chemical, biological and/or pharmaceutical analysis. Such an analysis system may be a fluid separation device, a liquid chromatography device, an electrophoresis system, or the like. In a realization of the apparatus as a device for chemical, biological and/or pharmaceutical analysis, functions like (protein) purification, electrophoresis investigation, fluid separation, or chromatography investigations may be realized by the analysis device. An example for a fluidic device is an apparatus of the 1100 Series for liquid chromatography (LC) of Agilent Technologies.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
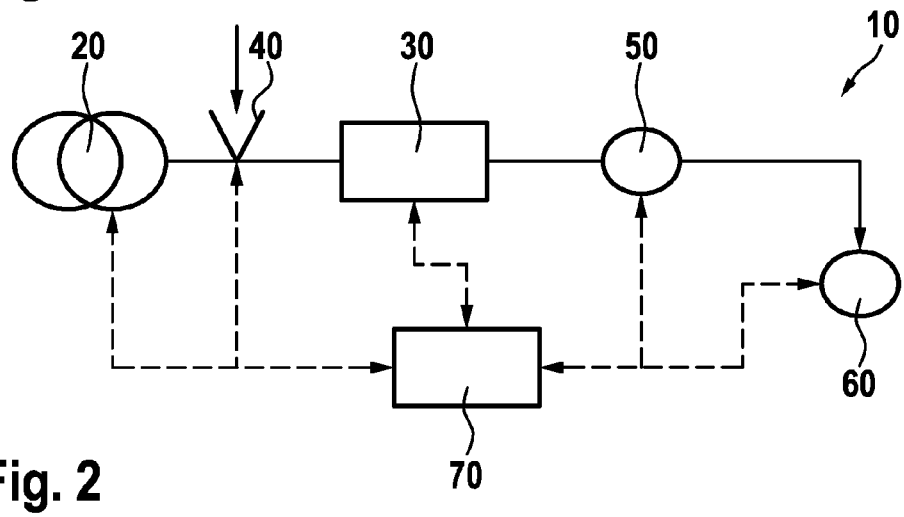
FIG. 1 shows a liquid separation system, in accordance with embodiments of the present invention, for instance used in high performance liquid chromatography (HPLC).

The illustration in the drawing is schematical.

Referring now in greater detail to the drawings, FIG. 1 depicts a general schematic of a liquid separation system 10. A pump 20—as a mobile phase drive—drives a mobile phase through a separating device 30 (such as a chromatographic column) comprising a stationary phase. A sampling unit 40 can be provided between the pump 20 and the separating device 30 in order to introduce a sample fluid to the mobile phase. The stationary phase of the separating device 30 is adapted for separating compounds of the sample liquid. A detector 50 is provided for detecting separated compounds of the sample fluid. A fractionating unit 60 can be provided for outputting separated compounds of sample fluid.

A data processing unit 70, which can be a PC or workstation, might be coupled (as indicated by the dotted arrows) to one or more of the devices in the liquid separation system 10 in order to receive information and/or control operation. For example, the data processing unit 70 might control operation of the pump 20 (for instance setting control parameters) and receive therefrom information regarding the actual working conditions (such as output pressure, flow rate, etc. at an outlet of the pump 20). The data processing unit 70 might also control operation of the sampling unit (for instance controlling an amount of sample being injected, controlling sample injection or synchronizing sample injection with operating conditions of the pump 20). The separating device 30 might also be controlled by the data processing unit 70 (for instance selecting a specific flow path or column, setting operation temperature, etc.), and send—in return—information (for instance operating conditions) to the data processing unit 70. Accordingly, the detector 50 might be controlled by the data processing unit 70, and send information (for instance about the detected sample compounds) to the data processing unit 70. The data processing unit 70 might also control operation of the fractionating unit 60 (for instance in conjunction with data received from the detector 50) and provide data back.

In the following, referring to FIG. 2, an apparatus 200 (which may be the data processing unit 70 or which may provide control commands to the data processing unit 70) for determining an operation mode of the fluidic device 10 according to an exemplary embodiment will be explained.

The fluidic device 10 modeled with or controlled by the apparatus 200 is capable of mixing multiple components of a solvent at a source position of the fluidic device 10 at which the individual components of the solvent are supplied, for instance from bottles or vials (not shown). The fluidic device 10 will, supported by one or more pumps 20, transport the mixture of the solvent constituents to a destination position such as an inlet of the chromatographic column 30.

The apparatus 200 comprises an input/output unit 202 via which a user may input data 204 into the system. The input data 204 may include instructions for controlling performance of the apparatus 200 and may additionally or alternatively also include data parameters used for an analysis or design of a performance of the modeled fluidic device 10.

Optionally, such input data 204 may be supplied to an admissibility verification unit 206 adapted for verifying whether selection of the input data 204 or a manipulation thereof by a user is admissible in view of physical frame conditions of the system 10. If this is the case, admitted parameters 205 are forwarded to a determination unit 208 which will be explained below in more detail. If this is not the case, the admissibility verification unit 206 will reject the parameters 204 and will provide a corresponding feedback signal 210 to the input/output unit 202 so that it is indicated to the user that the input data 204 is not in accordance with the requirement of system 10, for instance is not in accordance with laws of nature (for example when a negative conduit volume is adjusted by a user) or is not supported by the device 10 (for example when a pressure is adjusted which exceeds the maximum pumping capability of the pump 20).

The apparatus 200 further comprises the determining unit 208 adapted for determining the operation mode by defining for instance a time sequence according to which at least two fluidic components are supplied at the source position so that a target dependency of a concentration profile of the mixture is obtained at the destination position. In this example, the target time dependency represents a function of a varying concentration of the mixture over time. Such a time sequence calculated by the determination unit 208 may be supplied or fed back as operation mode data 211 to the input/output unit 202 so that a user can see which recipe or solvent supply algorithm of supplying the components of the solvent is necessary so that the defined target dependency defined by the user via the input data 204 can be obtained. Thus, a user simply defines via the input/output unit 202 which actual solvent composition over time is desired at the target destination, and the system 200 will automatically calculate parameters 213 (in machine language) to be input to the fluidic device 10 so that the desired time sequence is obtained actually in practice, for instance compensating parasitic effects within the device 10. For performing this calculation, the determination unit 208 may use a preknown parameterization or configuration of the fluidic device 10. This data can be obtained from a database 212 (such as a memory, for instance a hard disk) which is in bidirectional data exchange communication 214 with the determining unit 208. Thus, the database 212 may store data indicative of an operation or technical specification of the fluidic device 10. Optionally, the database 212 may also be in bidirectional data communication 216 with the input/output unit 202 to allow a user to download data from the database 212, or to allow the user, via the input/output unit 202, to store data regarding a measurement device in the database 212. Also the admissibility verification unit 206 is in bidirectional data communication with the database 212, as indicated by reference numeral 220.

Figure 2:
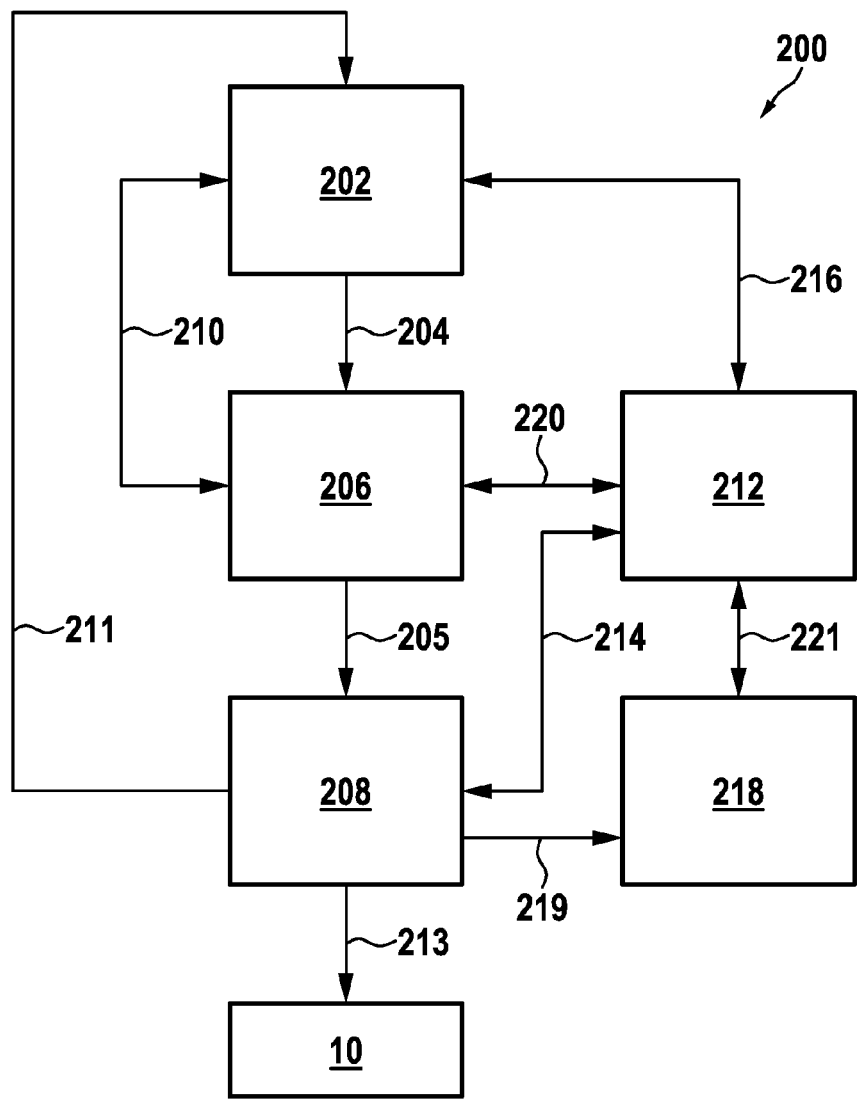
FIG. 2 shows a system for determining an operation mode of a fluidic device according to an exemplary embodiment.

As can further be taken from FIG. 2, additionally or alternatively to the provision of the data 210 to the input/output unit 202, the determination unit 208 may also supply this data or a sub-set 219 thereof as control data to a fluidic device 218 (such as a liquid chromatography device) as control parameters. Thus, when the determination unit 208 has determined the parameters required for an operation of the fluidic device 218 in such a manner that the desired method defined by the user is carried out, this data 219 can be directly used as control parameter machine language for correspondingly operating the fluidic device 218.

The parameterization of the fluidic device 218 taken into account by the determining unit 208 may include data such as size of the fluidic device 218 or components thereof, a volume of a fluidic conduit of the fluidic device 218, a pump performance by the fluidic device 218, delay parameters of operating the fluidic device, friction parameters considering frictional effects during operating the fluidic device 218 (which may be influenced by frictional parameters of walls of fluidic conduits of the fluidic device 218 or the like), a flushing performance of the fluidic device 218 (for instance a cleaning sequence applied to the fluidic device 218 before or after performing an experiment), a cooperation of different components of the fluidic device (such as the cooperation of different pumps of the fluidic device 218), etc. To supply information regarding the parameterization of the fluidic device 218 to the determining unit 208, the data communication path 210 may be bidirectional. The determining unit 208 may store data in the memory 212 or retrieve data from the memory 212. Also a direct data communication between the memory 212 and the fluidic device 218 may be possible, as indicated by reference numeral 221. Correspondingly, the determination unit 208 adjusts the operation mode of the fluidic device 218 including a definition of a procedure of separating different fractions of a fluidic sample mixed with the solvent mixed in accordance with the scheme defined by the determination unit 208. Thus, the instructions 219 may be sufficient for the fluidic device 218 to carry out a corresponding method.

The data 210 calculated by the determination unit 208 may be displayed via a graphical user interface of the input/output unit 202 allowing a user to manipulate the operation mode. Thus, an iterative feedback-based system may be provided which allows, in one or more iterations, a user to further to refine the adjusted operation mode of the fluidic device 218.

Within the determination unit 208, a model of the fluidic device 218 may be used in conjunction with the admitted parameters 205 as defined by the user so that data to be desired are fed in correspondence with an input sequence of multiple components of the solvent so that the system may compute analytically, numerically and/or phenomenologically how to supply the different components at the source position of the fluidic device 218 to obtain the desired time sequence at the target destination position.

In order to derive an actual configuration model empirically the fluidic device 218 can be fed with a test set of parameters, on which execution relevant data is generated by the fluidic device 218 (such as the liquid chromatography device 10 of FIG. 1) and fed into the configuration database 212. This way the data base 212 can be trained to know the actual behavior of the fluidic device 218. A possible solution to derive such knowledge is the extraction of a complex transfer function (complex output/complex input). The database 212 then validates this transfer function and stores this function or a descriptive set of data to have it available on request by the determination unit 208.

Figure 3:
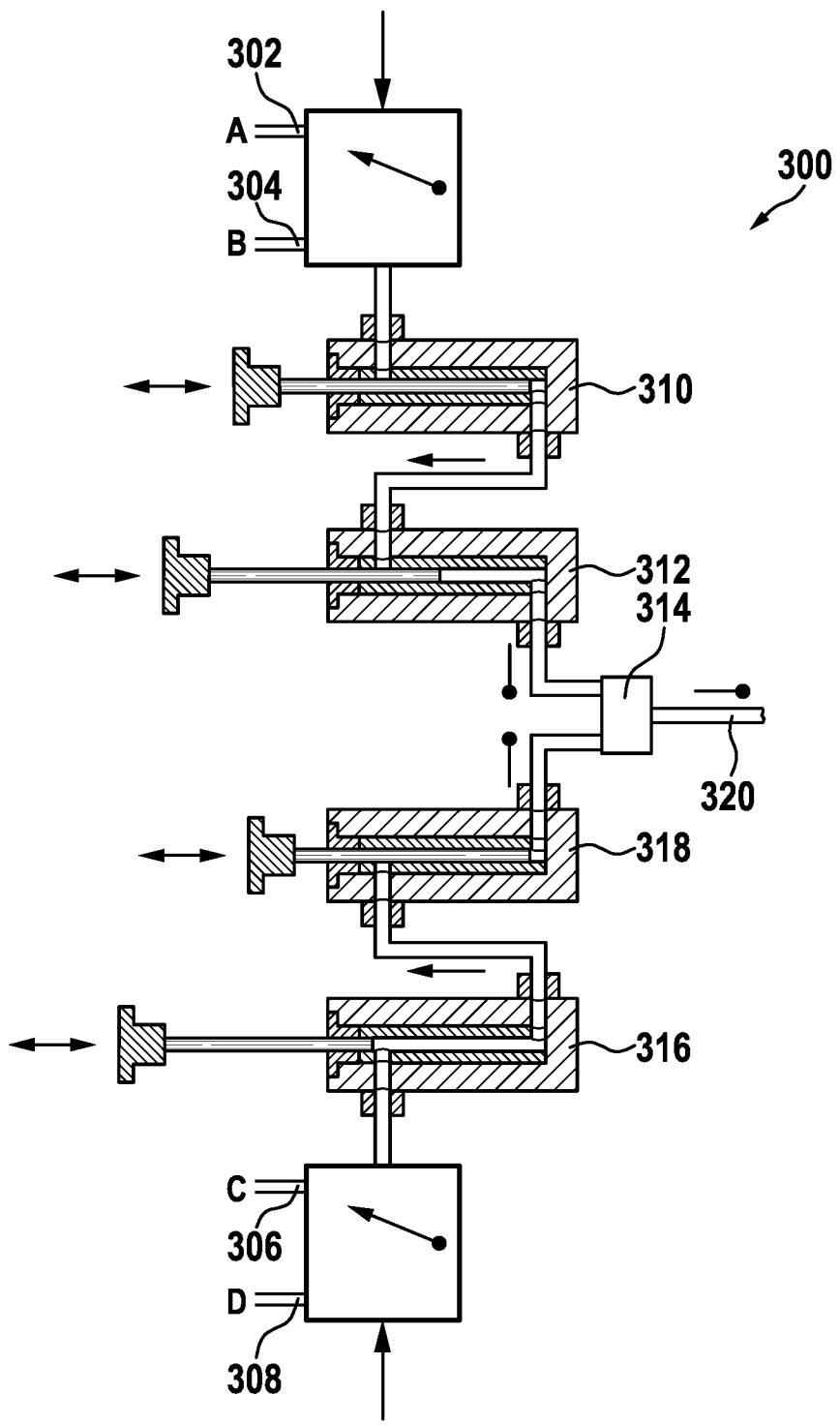
FIG. 3 illustrates a pump configuration with a quaternary pump of a fluidic device modeled according to an exemplary embodiment.

FIG. 3 illustrates a pump system 300 of the fluidic device 218.

At a first source position 302, a first component A of a solvent is supplied. At a second source position 304, a second component B is supplied. At a third source position 306, a third component C for the solvent is supplied. At a fourth source position 308, a fourth component D is provided. The components A and B are supplied to a first pump chamber 310 and subsequently to a second pump chamber 312 before being provided to a mixing unit or T-piece 314. The components supplied at source positions 306 and 308 are pumped by a third pump 316 and by a fourth pump 318 before being supplied to the mixing unit 314. An output of the mixing unit 320 including a mixture of at least a part of components selected from or combined of A, B, C, and D may be denoted as a destination position at which the system 300 is connected to a liquid chromatography separation column (not shown, but constituted in a similar manner as reference numeral 30 in FIG. 1) for subsequent LC analysis, for instance defining a gradient on the column 30.

For the determination performed by the determination unit 208, the system 300 is modeled in the apparatus 200 and the user defines which time dependency of the concentration is desired at the destination position 320 or downstream thereof, i.e. which solvent constitution should be supplied to the chromatographic column 30. The determination unit 208 will then perform a calculation considering the performance of the pumps 310, 312, 316, 318 as well as internal volumes of the various conduits in FIG. 3, temperature and velocity profiles within the conduits of the system 300, or the like as stored in the configuration data base 212 so as to calculate the data 210 indicating how (particularly when and in which amount) the different substances 302, 304, 306, 308 are to be supplied to obtain the desired target time dependency.

Thus, the complex pump configuration 300, which can also be any hybrid system including any desired n-ternary pump configuration (for instance a stack of two quaternary pumps) may be taken into account to set up an appropriate gradient for the chromatographic column 30.

Figure 4:
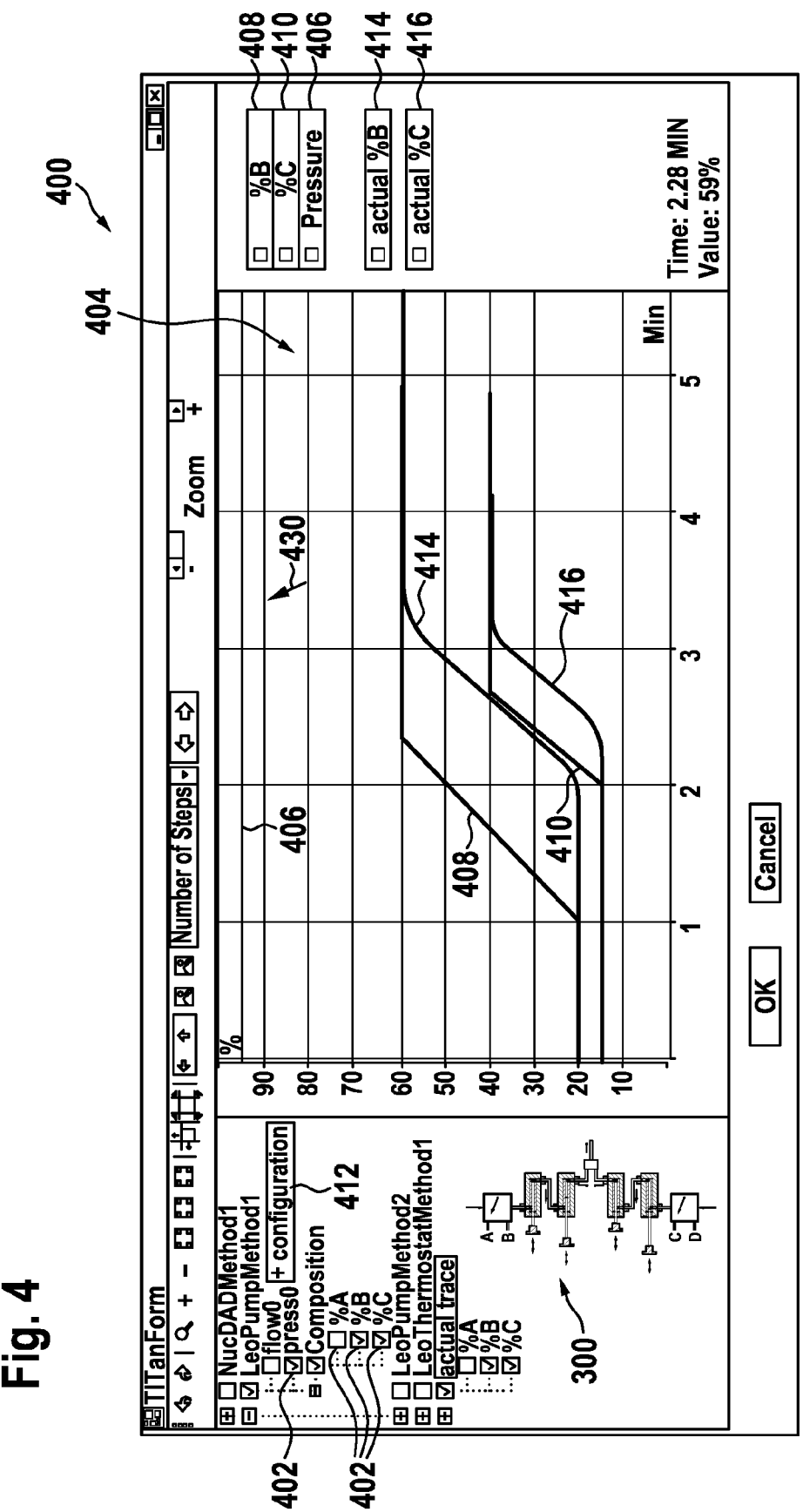
FIG. 4 illustrates a graphical user interface enabling a user for adjusting an operation mode of a liquid chromatography device according to an exemplary embodiment.

FIG. 4 shows a graphical user interface 400 according to an exemplary embodiment via which a user may define in an interactive manner a desired time sequence as to how the different components A, B, C, D (A not selected to be displayed and D not shown here) are to be provided at the destination position 320 and will receive information as to how the different components A, B, C, D are to be supplied at the source positions 302, 304, 306, 308 of the pump system 300 to obtain the desired result. The user interface 400 comprises a number of check fields 402 (each of which being activatable or deactivatable by a mouse click) via which a number of parameters can be adjusted for the simulation displayed in a diagram 404. For instance, it can be adjusted which constituents of the solvent A, B, C, D should be taken into account for a specific application. In the diagram 404, a number of graphs are then plotted showing programmed values of the corresponding solvent concentrations at the source destination and corresponding actual values at the target destination which can be obtained when considering realistic effects within the device 300.

For instance, the diagram 404 shows a pressure curve 406 indicative of the pressure conditions within the system 300. Furthermore, for the present scenario of FIG. 4 that only components A, B and C are mixed, a first ideal concentration curve 408 regarding component B is plotted (for instance ramping from 20% to 60%). Moreover, a second ideal concentration curve 410 regarding component C is plotted. The ideal curves 408, 410 are angled and are indicative of a linear increase of the corresponding partial concentrations between time intervals during which the corresponding partial concentrations remain constant. Considering a configuration 412 of the system 300, i.e. the technical parameters of the physical device 300 stored in the database 212, an actual or real curve 414 of the concentration of constituent B is obtained which corresponds to the ideal curve 408. In a similar manner, the actual conditions of the concentration profile of component C are plotted as a curve 416 which corresponds to the ideal curve 410.

For instance, when the time dependence of supplying the component B is adjusted for the device 300 in accordance with curve 408, at the destination of the device 300 the curve 414 is obtained. When the concentration of the component C is adjusted in accordance with curve 410 at the corresponding source, the profile 416 is obtained at the destination. Thus, with the user interface 400, a user can see as to how the pump configuration 300 has an effect on the actual constituent of the components B and C. Then, using a mouse pointer 430 operated by a computer mouse or the like, the user may manipulate the individual curves in the diagram 404 until a desired actual sequence is obtained.

According to an exemplary embodiment, the user will simply define as to how the target curves 414, 416 shall look like, and the system 400 may then automatically calculate curves 408, 410 telling a user as to how to provide the different components B, C at the input or source positions to obtain the desired result, or vice versa.

Figure 5:
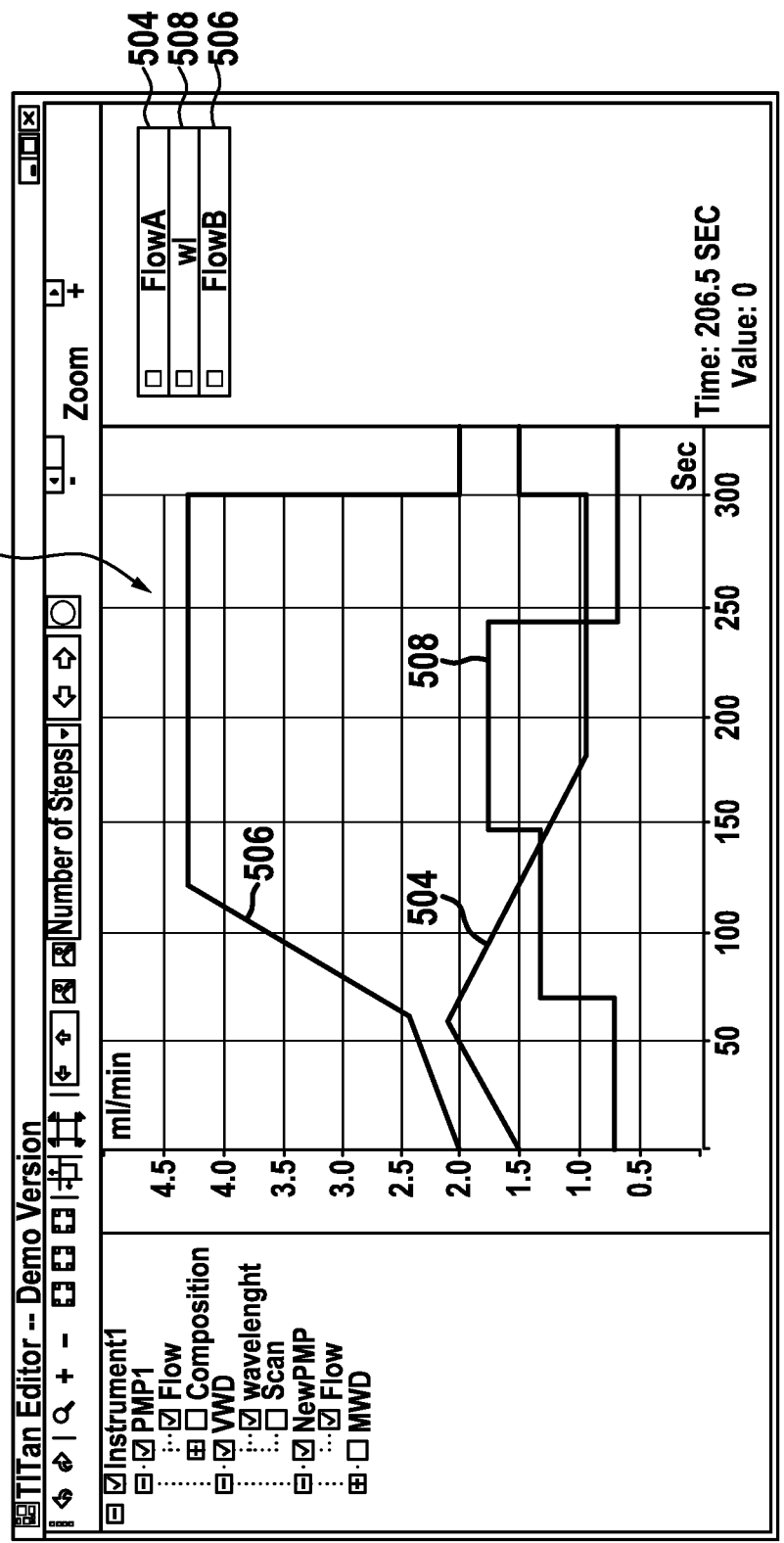
FIG. 5 and FIG. 6 show screenshots of a graphical user interface allowing to manipulate a graph.
Figure 6:
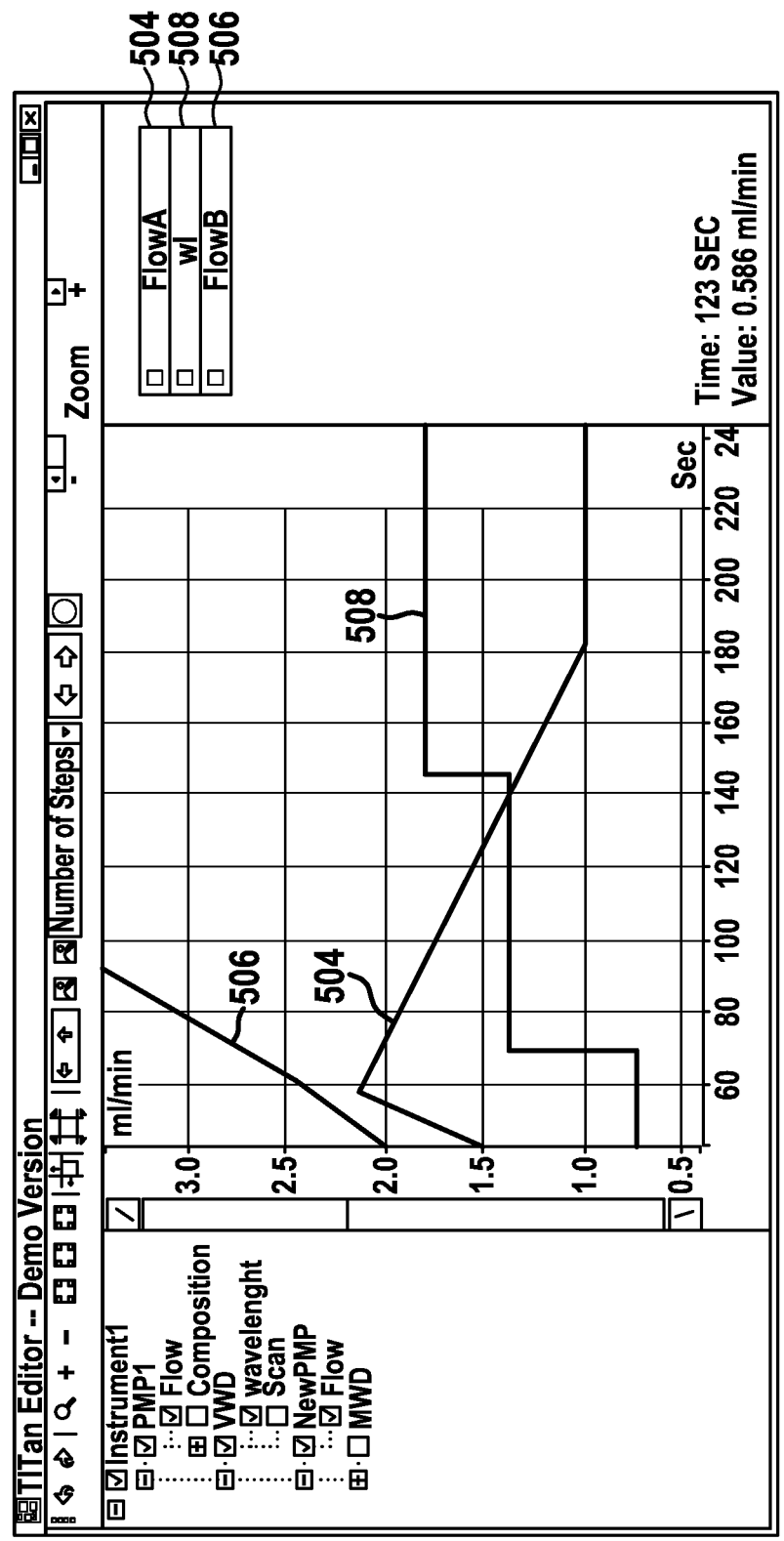

FIG. 5 shows a screenshot 500 of a user interface according to an exemplary embodiment illustrating a diagram 502 including a flow of a first component A 504, a flow of a second component B 506 and a third control parameter 'wl' 508 (measurement wavelength of a variable wavelength detector [VWD]). As can be taken from a comparison with a screenshot 600 shown in FIG. 6, the user interface provides the opportunity to overlay graphs from every module to view or edit them at once. Furthermore, zoom and scroll functions are provided for viewing at a higher resolution.

Figure 7:
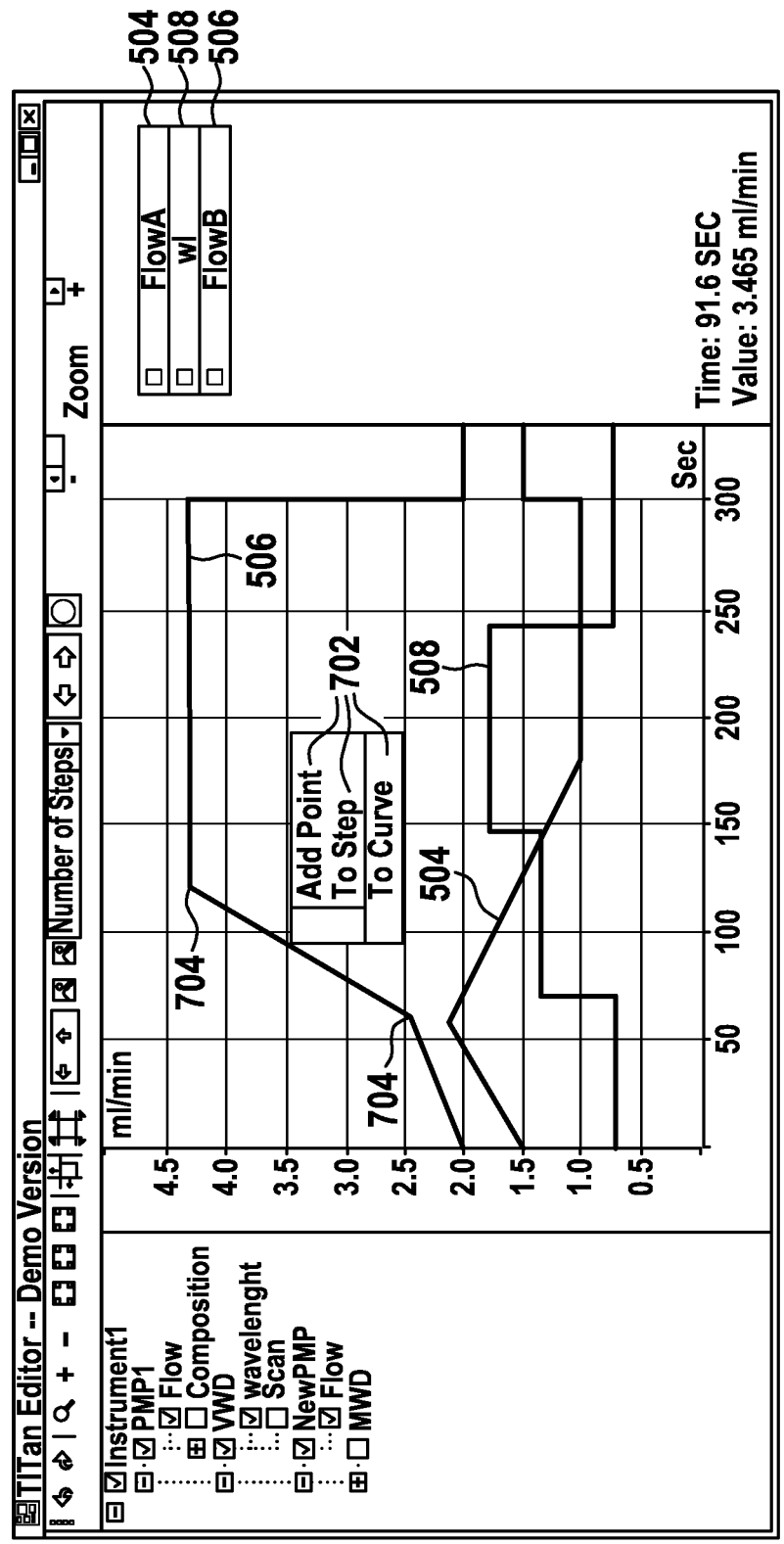
FIG. 7 and FIG. 8 show modifications of a graph adjustable with a user interface according to an exemplary embodiment.
Figure 8:
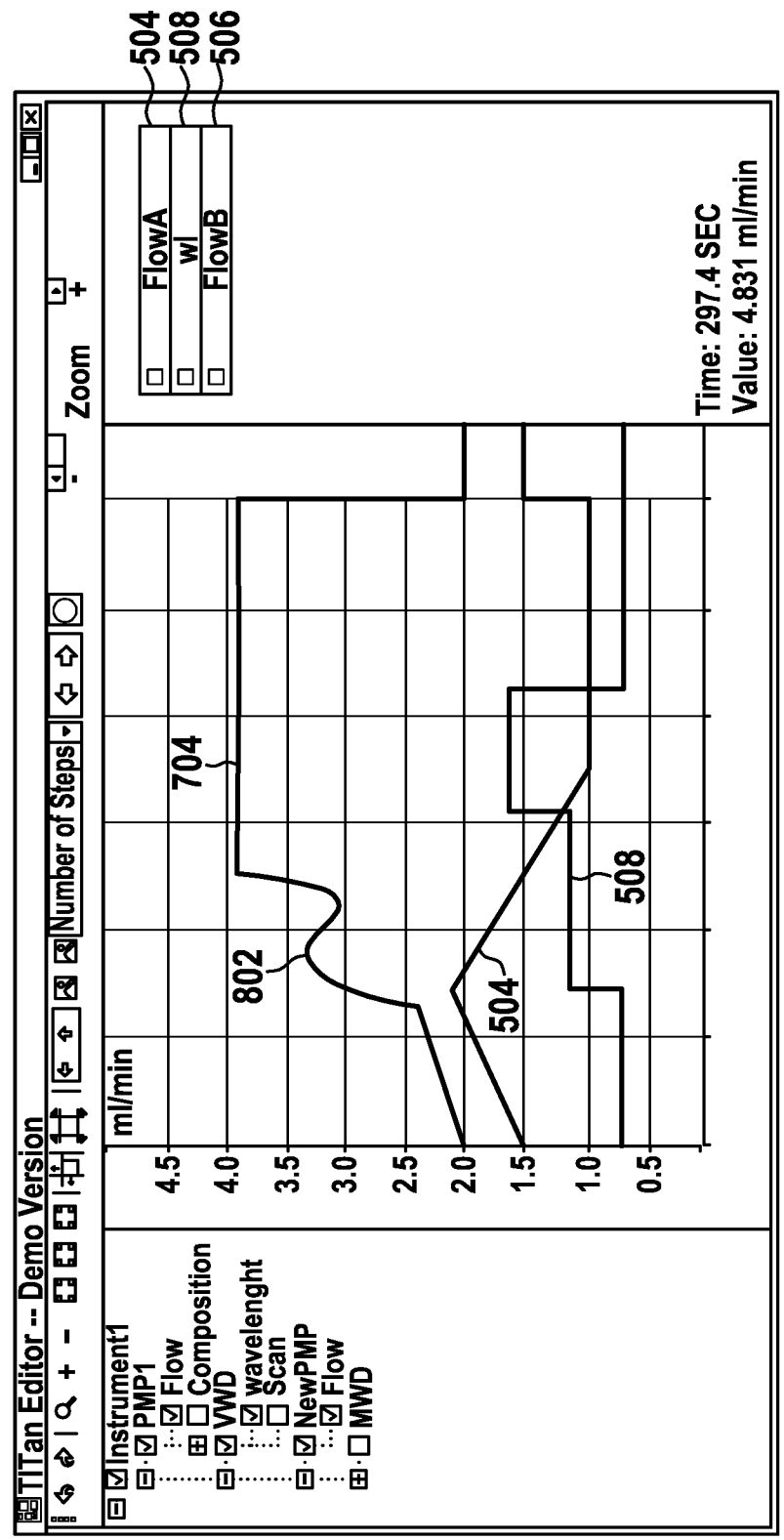

A screenshot 700 illustrated in FIG. 7 shows that modifications like add, delete or change allow a user to comfortably add or delete points or change the interpolation style for instance by a right click at a wanted location. Created points can be dragged to new coordinates. For such purposes, the user may select one of control fields 702. As can be taken from a screenshot 800 shown in FIG. 8, the user may eliminate edges in a section 704 in the graph when changing interpolating style from linear sections to curves, for instance using Bezier curves 802.

For empirically extracting actual physical behavior of a device different methods exist which can be implemented according to exemplary embodiments to model delay volume (or dwell volume, gradient volume, transition volume) which is presently considered as one of the main origins of a discrepancy between a target value and an actually achieved value of a concentration provided by a pump device such as a pump device 300.

The dwell volume may be denoted as the system volume from the point of the mobile phase mixing to the target destination, for instance at the column head. Different dwell volumes may result in a time shift (i.e. the time for the mobile phase to reach the column head). Additionally, the dwell volume may affect the gradient shape (dispersion effects, flush out behavior, etc.). Thus, the programmed gradient may become deteriorated. Even with a same delay volume, the chromatographs can look different on different systems. The dwell volume may have a more pronounced impact for narrow bore applications, especially combined with fast gradient.

According to one embodiment, dwell volume determination may be done in a way as disclosed by John W. Dolan, "Dwell Volume Revisited", LCGC North America. Volume 24, No. 5, May 2006, pages 458 to 466. In accordance with this, it is possible to measure the dwell time by drawing a tangent to a main part of the gradient curve and extend the baseline to intersect this tangent. The time it takes from the start of the program to this intersection may be denoted as the dwell time. This may be multiplied with the flow rate to get the dwell volume. The corresponding disclosure of Dolan 2006 is incorporated by reference.

According to another exemplary embodiment, calculation of the dwell volume may be performed on a step of a gradient, not on a linear gradient. With such an embodiment, the delay volume is close to the physical volume (when the gradient starts to hit the column). Transition volumes reflect the dispersion effects (i.e. how much a program gradient becomes deteriorated). Such a dwell volume calculation which may be implemented according to an exemplary embodiment, is disclosed by G. Hendriks et al. "New practical algorithm for modeling retention times in gradient reversed-phase high-performance liquid chromatography", Journal of Chromatography A, 1089 (2005), pages 193 to 202. The corresponding disclosure of Hendriks 2005 is incorporated by reference.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. An apparatus for determining an operation mode of a fluidic device wherein the fluidic device is capable of adjusting a fluid composition at a first position to correspondingly influence a fluid composition at a second position located downstream from the first position, the apparatus comprising:
   a determining unit adapted for determining the operation mode by identifying a target time-dependency of a concentration profile of at least two different liquid components in the fluid composition at the second position, determining a time sequence for separately supplying variable amounts of the at least two different liquid components to the fluidic device at the first position based on the target time-dependency, and automatically generating operating parameters for the fluidic device according to the determined time sequence.

2. The apparatus of claim 1,
   wherein the fluidic device is capable of supplying a fluid with a definable temperature at the first position and is capable of transporting the fluid to the second position, and
   wherein the determining unit is adapted for determining the operation mode by defining a temperature profile of supplying the fluid at the first position so that a target time-dependency of a temperature profile of the fluid is obtained for the second position, the target time dependency representing a temperature variation of the fluid over time.

3. The apparatus of claim 1,
   wherein the fluidic device is capable of supplying a fluid with a definable flow profile at the first position and is capable of transporting the fluid to the second position, and
   wherein the determining unit is adapted for determining the operation mode by defining a flow profile of supplying the fluid at the first position so that a target time-dependency of a flow profile of the fluid is obtained for the second position, the target time-dependency representing a flow variation of the fluid over time.

4. The apparatus of claim 1, wherein the determining unit is adapted for determining the operation mode under consideration of a preknown parameterization of the fluidic device.

5. The apparatus of claim 4, wherein the parameterization defines physical properties of the fluidic device.

6. The apparatus of claim 4, wherein the parameterization defines at least one physical property of the group consisting of a size of the fluidic device, a volume of a fluid conduit of the fluidic device, a pump performance of the fluidic device, a delay parameter of operating the fluidic device, a friction parameter of operating the fluidic device, a flush performance of the fluidic device, and a cooperation of different components of the fluidic device.

7. The apparatus of claim 1, wherein
   the operation mode defines at least one of the group consisting of a procedure of separating different components of fluids by the device, a procedure of analyzing a medication, a procedure of analyzing a biological sample, a procedure of mixing various fluids, a diagnostic procedure, a procedure requiring official approval, a procedure of flushing the device, a selection of a solvent composition for the device, a procedure of applying a concentration gradient to the fluidic device, and a selection of an operation temperature for the fluidic device;
   the operation mode defines a sequence of instructions providable to the device for operating the fluidic device;
   the operation mode is a chromatographic method of operating a chromatography device;
   the determining unit processor is adapted for performing the determination by physically modeling procedures taking place in the fluidic device;
   the determining unit processor is adapted for performing the determination by simulating procedures taking place in the fluidic device; or
   the determining unit processor is adapted for performing the determination under consideration of physical laws.

8. The apparatus of claim 1, further comprising a user interface adapted for displaying an operation mode of the fluidic device on a display device.

9. The apparatus of claim 8, wherein
the user interface is adapted for displaying the operation mode as graphs;
the user interface is adapted for enabling a user to manipulate the operation mode;
the user interface is adapted for enabling a user to manipulate the operation mode, wherein the user interface and the determining unit are adapted for updating or tracking a part of the operation mode upon manipulation of another part of the operation mode by the user;
the user interface is adapted to enable the user to define the target time-dependency;
the user interface is adapted for enabling a user to manipulate the operation mode, wherein the user interface is adapted to provide a visual feedback to the user in response to a modification of the operation mode;
the user interface is a graphical user interface; or
the user interface is adapted for displaying simultaneously both the time sequence and the target time-dependency.

10. The apparatus of claim 1, wherein the determining unit is adapted for determining an operation mode of the fluidic device as an actual operation mode by substituting one of a straight curve section and an angled curve section by a rounded curve section to simulate a physical effect.

11. The apparatus of claim 10, wherein the determining unit is adapted for performing the substitution in accordance with a physical model of a process relating to the straight curve section or the angled curve section.

12. The apparatus of claim 10, wherein the determining unit is adapted for performing the substitution by calculating a Bezier curve.

13. The apparatus of claim 9, further comprising an admissibility verification unit adapted for verifying whether a manipulation by a user is admissible in view of physical frame conditions.

14. The apparatus of claim 13, wherein the admissibility verification unit is adapted for rejecting the manipulation by the user upon determining that the manipulation is not in accordance with physical frame conditions.

15. The apparatus of claim 14, wherein the admissibility verification unit is adapted for providing feedback to the user when rejecting the manipulation by the user, the feedback including a notice that the manipulation is not in accordance with physical frame conditions.

16. The apparatus of claim 1, wherein the fluidic device is one of the group consisting of fluid separation device adapted for separating compounds of a fluid, a fluid purification device, a measurement device, a life science device, a sensor device, a device for chemical, biological and/or pharmaceutical analysis, a capillary electrochromatography device, a capillary electrophoresis device, a liquid chromatography device, an HPLC device, a gas chromatography device, and a mass spectroscopy device.

17. A method of determining an operation mode of a fluidic device, wherein the fluidic device is capable of adjusting a fluid composition at a first position to correspondingly influence a fluid composition at a second position located downstream from the first position, the method comprising:
identifying a target time-dependency of a concentration profile of at least two different liquid components in the fluid composition at the second position;
determining a time sequence for separately supplying variable amounts of at the least two different liquid components to the fluidic device at the first position based on the target time-dependency, and
automatically generating operating parameters for the fluidic device according to the determined time sequence.

18. A computer program product comprising instructions stored on a non-transitory computer-readable medium, for executing the method of claim 17, when run on a data processing system.

* * * * *

UNITED STATES PATENT AND TRADEMARK OFFICE
CERTIFICATE OF CORRECTION

PATENT NO.         : 8,515,587 B2  
APPLICATION NO.    : 12/234621  
DATED              : August 20, 2013  
INVENTOR(S)        : Klaus Witt et al.

Page 1 of 1

It is certified that error appears in the above-identified patent and that said Letters Patent is hereby corrected as shown below:

In the Claims

In column 16, lines 13-14, in claim 2, delete "time dependency" and insert -- time-dependency --, therefor.

In column 18, line 27, in claim 17, delete "of at the" and insert -- of the at --, therefor.

Signed and Sealed this  
Third Day of December, 2013

Margaret A. Focarino  
*Commissioner for Patents of the United States Patent and Trademark Office*